(12) United States Patent
Bierman (10) Patent No.: US 8,585,655 B2
(45) Date of Patent: Nov. 19, 2013

(54) SECUREMENT DEVICE FOR I.V. T-CONNECTOR

(75) Inventor: Steven F. Bierman, Del Mar, CA (US)

(73) Assignee: Venetec International, Inc., Covington, GA (US)

( * ) Notice: Subject to any disclaimer, the term of this patent is extended or adjusted under 35 U.S.C. 154(b) by 1711 days.

(21) Appl. No.: 11/438,901

(22) Filed: May 23, 2006

(65) Prior Publication Data
US 2006/0270994 A1 Nov. 30, 2006

Related U.S. Application Data

(60) Provisional application No. 60/683,926, filed on May 23, 2005.

(51) Int. Cl.
*A61M 5/32* (2006.01)

(52) U.S. Cl.
USPC .......................................... 604/180; 604/174

(58) Field of Classification Search
USPC ................. 604/174, 177, 178, 180, 513, 533; 128/DIG. 6, DIG. 26
See application file for complete search history.

(56) References Cited

U.S. PATENT DOCUMENTS

| | | | |
|---|---|---|---|
| 2,402,306 A | 6/1946 | Turkel | |
| 2,525,398 A | 10/1950 | Collins | |
| 2,533,961 A | 12/1950 | Rousseau et al. | |
| 3,064,648 A | 11/1962 | Bujan | |
| 3,167,072 A | 1/1965 | Stone et al. | |
| 3,245,567 A | 4/1966 | Knight | |
| 3,394,954 A | 7/1968 | Sarns | |
| 3,529,597 A | 9/1970 | Fuzak | |
| 3,589,361 A | 6/1971 | Loper et al. | |
| 3,677,250 A | 7/1972 | Thomas | |
| 3,686,896 A | 8/1972 | Rutter | |
| 3,766,915 A | 10/1973 | Rychlik | |
| 3,812,851 A | 5/1974 | Rodriguez | |
| 3,834,380 A | 9/1974 | Boyd | |
| 3,856,020 A | 12/1974 | Kovac | |
| 3,863,631 A | 2/1975 | Baldwin | |
| 3,900,026 A | 8/1975 | Wagner | |

(Continued)

FOREIGN PATENT DOCUMENTS

| | | |
|---|---|---|
| DE | 2 341 297 | 4/1975 |
| EP | 0 114 677 | 5/1989 |

(Continued)

OTHER PUBLICATIONS

National Patent Services, Search Report re Patent Validity Study of U.S. Patent 5827230, pp. MDG 001319-MDG 001320, May 23, 2006.

Cravens, et al., Urinary Catheter Management, American Family Physician, vol. 61, No. 2, pp. MDG 000273-MDG 000282, Jan. 15, 2000.

(Continued)

*Primary Examiner* — Emily Schmidt
(74) *Attorney, Agent, or Firm* — Knobbe Martens Olson & Bear LLP (57) ABSTRACT

An anchoring system includes a simply-structured device which permits a portion of a catheter or similar medical article to be easily anchored to a patient, desirably without the use of tape or needles and suture. The anchoring system comprises an anchor pad and a retainer mounted upon the anchor pad. The retainer includes a plurality of intersecting channels into which the medical article to be retained is placed. The medical article is secured within the intersecting channels by retaining at least one axially extending member on the medical article.

8 Claims, 10 Drawing Sheets

(56) References Cited

U.S. PATENT DOCUMENTS

| | | |
|---|---|---|
| 3,906,946 A | 9/1975 | Nordstrom |
| 3,920,001 A | 11/1975 | Edwards |
| 3,942,228 A | 3/1976 | Buckman et al. |
| 3,973,565 A | 8/1976 | Steer |
| 4,004,586 A | 1/1977 | Christensen et al. |
| D243,477 S | 2/1977 | Cutruzzula et al. |
| 4,020,835 A | 5/1977 | Nordstrom et al. |
| 4,037,599 A | 7/1977 | Raulerson |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,161,177 A | 7/1979 | Fuchs |
| 4,170,993 A | 10/1979 | Alvarez |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,250,880 A | 2/1981 | Gordon |
| 4,275,721 A | 6/1981 | Olson |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,362,156 A | 12/1982 | Feller, Jr. et al. |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,516,968 A | 5/1985 | Marshall et al. |
| 4,561,857 A | 12/1985 | Sacks |
| 4,563,177 A | 1/1986 | Kamen |
| 4,585,435 A | 4/1986 | Vaillancourt |
| 4,585,444 A | 4/1986 | Harris |
| 4,631,056 A | 12/1986 | Dye |
| 4,633,863 A | 1/1987 | Filips et al. |
| 4,650,473 A | 3/1987 | Bartholomew et al. |
| 4,660,555 A | 4/1987 | Payton |
| 4,666,434 A | 5/1987 | Kaufman |
| 4,693,710 A | 9/1987 | McCool |
| 4,711,636 A | 12/1987 | Bierman |
| 4,723,948 A | 2/1988 | Clark et al. |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,792,163 A | 12/1988 | Kulle |
| 4,795,429 A | 1/1989 | Feldstein |
| 4,826,486 A | 5/1989 | Palsrok et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,878,897 A | 11/1989 | Katzin |
| 4,880,412 A | 11/1989 | Weiss |
| 4,897,082 A | 1/1990 | Erskine |
| 4,898,587 A | 2/1990 | Mera |
| 4,919,654 A | 4/1990 | Kalt |
| 4,934,375 A | 6/1990 | Cole et al. |
| 4,941,882 A | 7/1990 | Ward et al. |
| 4,955,864 A | 9/1990 | Hajduch |
| 4,966,582 A | 10/1990 | Sit et al. |
| 4,976,700 A | 12/1990 | Tollini |
| 4,981,469 A | 1/1991 | Whitehouse et al. |
| 4,997,421 A | 3/1991 | Palsrok et al. |
| 5,024,665 A | 6/1991 | Kaufman |
| 5,037,397 A | 8/1991 | Kalt et al. |
| 5,037,398 A | 8/1991 | Buchanan |
| 5,037,405 A | 8/1991 | Crosby |
| D323,390 S | 1/1992 | Paine et al. |
| 5,084,026 A | 1/1992 | Shapiro |
| 5,098,048 A | 3/1992 | Chen |
| 5,105,807 A | 4/1992 | Kahn et al. |
| 5,112,313 A | 5/1992 | Sallee |
| 5,120,320 A | 6/1992 | Fayngold |
| 5,135,506 A | 8/1992 | Gentelia et al. |
| 5,137,519 A | 8/1992 | Littrell et al. |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,248,306 A | 9/1993 | Clark et al. |
| 5,263,943 A | 11/1993 | Vanderbrook |
| 5,267,967 A | 12/1993 | Schneider |
| 5,290,248 A | 3/1994 | Bierman |
| 5,314,411 A * | 5/1994 | Bierman et al. ............... 604/174 |
| 5,336,195 A | 8/1994 | Daneshvar |
| 5,344,414 A | 9/1994 | Lopez et al. |
| 5,354,282 A | 10/1994 | Bierman |
| 5,356,379 A * | 10/1994 | Vaillancourt ................... 604/80 |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,395,344 A | 3/1995 | Beisang, III et al. |
| 5,413,562 A | 5/1995 | Swauger |
| 5,456,671 A | 10/1995 | Bierman |
| 5,470,321 A | 11/1995 | Forster et al. |
| 5,484,425 A | 1/1996 | Fischell et al. |
| 5,496,283 A | 3/1996 | Alexander |
| 5,507,535 A | 4/1996 | McKamey et al. |
| 5,531,695 A | 7/1996 | Swisher |
| 5,578,013 A | 11/1996 | Bierman |
| 5,620,427 A | 4/1997 | Werschmidt et al. |
| 5,626,565 A | 5/1997 | Landis et al. |
| 5,643,217 A | 7/1997 | Dobkin |
| 5,681,290 A | 10/1997 | Alexander |
| 5,685,859 A | 11/1997 | Kornerup |
| 5,690,617 A | 11/1997 | Wright |
| 5,702,371 A | 12/1997 | Bierman |
| 5,755,225 A | 5/1998 | Hutson |
| 5,810,781 A | 9/1998 | Bierman |
| 5,827,230 A | 10/1998 | Bierman |
| 5,833,667 A | 11/1998 | Bierman |
| 5,885,251 A | 3/1999 | Luther |
| 5,947,931 A | 9/1999 | Bierman |
| 6,113,577 A | 9/2000 | Hakky et al. |
| D433,503 S | 11/2000 | Powers et al. |
| 6,213,979 B1 | 4/2001 | Bierman |
| 6,213,996 B1 | 4/2001 | Jepson et al. |
| 6,228,064 B1 | 5/2001 | Abita et al. |
| 6,231,548 B1 | 5/2001 | Bassett |
| 6,290,676 B1 | 9/2001 | Bierman |
| 6,332,874 B1 | 12/2001 | Eliasen et al. |
| 6,428,515 B1 | 8/2002 | Bierman et al. |
| 6,673,046 B2 | 1/2004 | Bierman et al. |

FOREIGN PATENT DOCUMENTS

| | | |
|---|---|---|
| EP | 0 356 683 | 7/1989 |
| EP | 0 169 704 | 11/1989 |
| EP | 0 367 549 | 5/1990 |

(56) References Cited

FOREIGN PATENT DOCUMENTS

| | | |
|---|---|---|
| EP | 0 263 789 | 6/1991 |
| EP | 0 247 590 | 12/1993 |
| EP | 0 720 836 | 7/1996 |
| GB | 2 063 679 | 6/1981 |
| GB | 2 086 466 | 5/1982 |
| GB | 2 178 811 | 2/1987 |
| WO | WO 90/05559 | 5/1990 |
| WO | WO 2004016309 A2 * | 2/2004 |

OTHER PUBLICATIONS

Dale® Foley Catheter Holder brochure, pp. MDG 000344-MDG 000346, 2002.

Grip-Lok Universal Tubing Securement brochure, pp. MDG 000364-MDG 000366, 2005-2006.

Expert Discusses Strategies to Prevent CAUTIs, Infection Control Today, pp. MDG 000603-MDG-000609, Jun. 2005.

* cited by examiner

SECUREMENT DEVICE FOR I.V. T-CONNECTOR

RELATED APPLICATIONS

This application claims the benefit of U.S. Provisional Patent No. 60/683,926, filed May 23, 2005, which is hereby incorporated by reference in its entirety.

BACKGROUND OF THE INVENTION

1. Field of the Invention

The present invention relates in general to a medical article anchoring system. In one mode, the present invention involves a catheterization system that interconnects an indwelling catheter with medical tubing and securely anchors the interconnection to a patient's skin.

2. Description of the Related Art

Medical treatment of patients commonly involves the use of percutaneously inserted catheters to deliver fluids directly into the bloodstream, a specific organ or an internal location within the patient, or to monitor vital functions of the patient. For instance, short, peripherally-inserted, intra-arteriovenous catheters are commonly used to direct fluids and/or medications directly into the bloodstream of the patient.

The fluid (e.g., parenteral liquid, medication, etc.) typically drains from a container positioned above the patient to feed under gravity or is delivered via an infusion pump. The fluid flows through tubing and thence into the indwelling catheter. The catheter and the fluid tubing are commonly removably attached to each other by a conventional t-connection.

A t-connection generally includes a male connector with a tapered conical portion that is adapted to fit into a correspondingly shaped receptacle of a female connector (i.e., a hub). A spin nut is commonly disposed on the male connector and is rotatable relative to the tapered conical portion. The spin nut includes internal threads that are adapted to engage external threads on the female connector to lock together the connectors. When properly engaged, theconical portion fits tightly within the receptacle to produce a sealed interconnection.

A healthcare provider can experience difficulty at times breaking the seal between the engaged conical portion and the hub of the t-connectors when disconnecting the male connector from the female connector. In order to aid such disconnection, some t-connectors include spin nuts that can slide axially between a distal position, in which the spin nut can freely rotate relative to the coupled connectors, and a proximal position, in which the spin nut and male connector are rotationally locked. The rotational lock is provided to assist in breaking the sealed coupling between the corresponding surfaces of the conical portion and the hub of the interengaged connectors.

The catheterization process often requires relatively frequent disconnection between the catheter and the fluid supply tube, as well as dressing changes. For instance, intravenous catheterization is frequently maintained for several days, depending upon the condition of the patient. The tubing is generally replaced every 48 to 72 hours in order to maintain the sterility of the fluid and the free-flow of the fluid through the tubing. A healthcare provider thus must frequently change the tubing and re-tape the connection. The healthcare provider also must frequently clean the insertion site about the indwelling catheter and change the dressings. Moreover, the tape, which secures the catheter to the skin of the patient, often covers the cannula insertion point. The healthcare provider must remove the tape to inspect the insertion point for inflammation or infection.

The traditional method of intravenous catheter securement—surgical tape and transparent dressings alone—have not always prevented catheter migration and/or dislodgment. Taped intravenous catheters are also easily pulled out during a "routine" dressing change, especially by inexperienced healthcare providers. And if the catheter migrates too far or dislodgment occurs, the healthcare provider must replace the catheter, thus exacerbating the time and expense required to maintain the intravenous feed. Such catheter re-starts also pose the risk of needle stick to the healthcare provider.

Prior securement methods have not served the patient as well. Surgical tape or foam strips are uncomfortable. Many patients also do not rest comfortably and worry about catheter dislodgment when they move, when only tape and a dressing secure the catheter in place.

Several additional drawbacks result from the use of tape to stabilize the catheter. One is contamination. Healthcare providers often tear off small strips of tape and place them on the hand rail on the patient's bed. Clostridium and other bacteria commonly exist on these surfaces and can be transferred to the patient's skin in the proximity of the insertion site.

In addition, tape securement requires the healthcare provider to handle the tape while wearing protective latex gloves. Tearing adhesive tape tends to produce microscopic and/or visible holes in the gloves and thus destroys glove barrier protection.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

An aspect of the invention is a securement device for anchoring a medical article having a first tubular body and a second tubular body connected to and extending from the first tubular body. The second tubular body is in fluidic communication with the first tubular body. The securement device comprises a retainer having a body member that has a first channel section formed through the body member. The first channel is configured to retain at least a portion of the first tubular body of the medical article and has a longitudinal access opening disposed along a longitudinal axis of the body member to allow at least ingress of the retained portion of the first tubular body into the first channel section. The body member further comprises a second channel section formed through at least a portion of the body member and intersects with the first channel section. The second channel section is configured to retain at least a portion of the second tubular body of the medical device and has an access opening disposed generally normal to the longitudinal axis to allow at least ingress of the retained portion of the second tubular body into the second channel portion. The body member further comprises a first abutment surface formed along the first channel and lying generally normal to the longitudinal axis of the body member and a second abutment surface formed along the second channel and lying generally normal to the longitudinal axis of the body member. The second abutment surface is spaced longitudinally apart from the first abutment surface by at least a distance that generally corresponds to a longitudinal width of the second tubular body.

Another aspect of the invention is a catheterization system that comprises a catheter connector that includes a first tubular body and a second tubular body attached to the first tubular body. The first tubular body is in fluidic communication with the second tubular body. The catheterization system further comprises a retainer having a proximal body portion and a distal body portion. The retainer further comprises a first channel extending through the proximal body portion and the distal body portion along a longitudinal axis. The first channel is configured to retain at least a portion of the first tubular body and has a longitudinal access opening to allow at least ingress of the first tubular body into the first channel. The retainer further comprises a second channel intersecting with the first channel and lying between the proximal and distal body portions. The second channel is configured to retain at least a portion of the second tubular body and has an access opening to allow at least ingress of the second tubular body into the second channel. The retainer further comprises a first abutment surface disposed on the proximal body portion of the retainer and a second abutment surface disposed on the distal body portion, each of the first and second abutment surfaces lying generally normal to the longitudinal axis. The catheterization system further comprises an anchor pad including upper and lower sides. The retainer is disposed on the upper side of the anchor pad, and the lower side of the anchor pad includes an adhesive surface to secure the retainer to the skin of a patient.

Still another aspect of the invention is an anchoring system for securely anchoring to a patient a medical article of the type having an elongated body including first and second elongated tubular bodies. The second elongated tubular body intersects with the first elongated tubular body. The anchoring system comprises a retainer including a body and first and second channels extending through at least a portion of the body. The channels are configured to accept at least a portion of the first and second elongated tubular bodies of the madical article. The anchoring system further comprises means for capturing both the first and second tubular bodies within the retainer body so as to arrest movement of the medical article relative to the retainer and an anchor pad having two sides, the retainer being mounted on one side and the other side including a layer of adhesive.

Yet another aspect of the invention is a retainer for securing a t-connector including at least first and second tubular members in flow communication with one another. The retainer comprises a first channel for receiving the t-connector without regard to the orientation of the second tubular member so that the second tubular member may be in any of a plurality of radial positions with respect to an axis through the first channel. The second tubular member being in a first position of the plurality of positions, being in a second position of the plurality of positions when rotated from the first position by approximately 180 degrees, and being in a third position of the plurality of positions when rotated from the first position by approximately 90 degrees. The retainer further comprises a first pair of abutment surfaces longitudinally restraining the first tubular member in both longitudinal directions when the second tubular member is in the first position and a second pair of abutment surfaces longitudinally restraining the first tubular member in both longitudinal directions when the second tubular member is in the second position. The second pair of abutment surfaces is different than the first pair of abutment surfaces. The retainer further comprises an abutment surface longitudinally restraining the first tubular member in a longitudinal direction when the second tubular member is in the third position. The abutment surface is different than the first and second pairs of abutment surfaces.

BRIEF DESCRIPTION OF THE DRAWINGS

The preferred embodiments will now be described with reference to the drawings. The drawings contain the following figures.

DETAILED DESCRIPTION OF THE PREFERRED EMBODIMENTS

The present embodiment of the medical article anchoring system is disclosed in the context of a catheterization system, and in particular in the context of a catheterization system utilizing a t-connector. The catheterization system also can include a catheter, a tube extension set and/or dressing materials.

The principles of the present invention, however, are not limited to catheters or to the specific type of t-connector disclosed. Instead, it will be understood by one of skill in this art, in view of the present disclosure, that the anchoring system disclosed herein also can be successfully utilized in connection with other types of t-connectors. In addition, it will be understood by one of skill in this art that the anchoring system disclosed herein also can be successfully utilized in connection with other types of medical articles, including other types of catheters, fluid drainage and delivery tubes. For example, but without limitation, the retainer disclosed herein can be configured to secure peripheral catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art may also find additional applications for the devices and systems disclosed herein.

Figure 1:
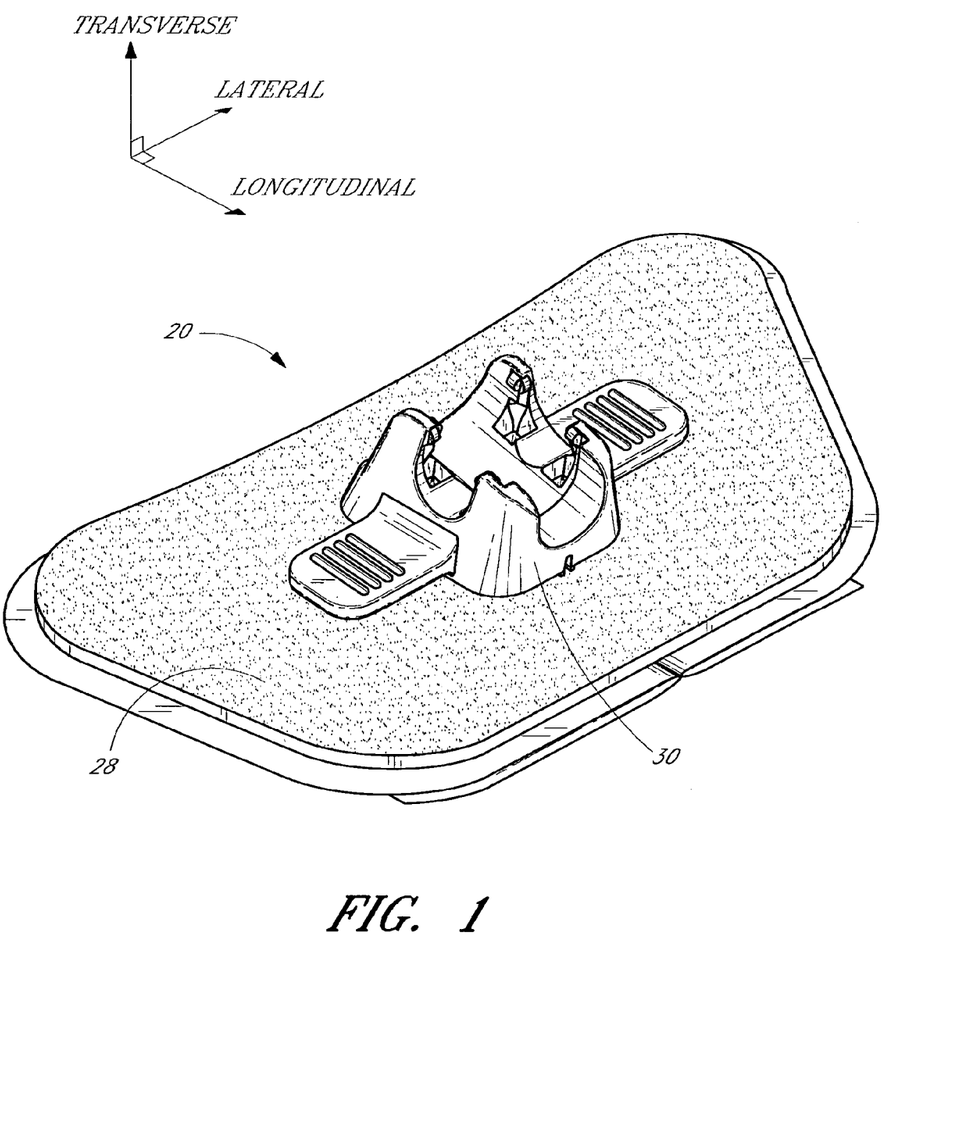
FIG. 1 is a perspective view of a catheterization system in accordance with a preferred embodiment of the present invention.

With reference now to the preferred embodiment, FIG. 1 illustrates in perspective view a catheter anchoring system 20. The anchoring system 20 cooperates with a t-connector (see FIG. 11) that securely connects a tube (e.g., a fluid supply line) to an indwelling catheter. The cooperation between the anchoring system 20 and the t-connector 22 maintains the catheter in the desired indwelling position.

The anchoring system 20 principally comprises a flexible anchor pad 28 having an adhesive bottom side that attaches to the skin of a patient. The pad 28 can be attached at any number of locations on a patient's body. For example, the anchoring system 20 could be located on the back of a patient's hand. The anchoring system can be used for catheterization at other locations on the patient's body, e.g., on the medial side of the wrist in connection with catheterization of a radial artery or on the anterior or posterior of the patient's torso in connection with epidural catheterization. The pad 28 supports a retainer 30. The retainer 30 in turn is configured to receive and secure in place the t-connector 22.

To assist in the description of the components of the anchoring system 20, the following coordinate terms are used (see FIG. 1). A "longitudinal axis" is generally parallel to the channel of the anchoring system 20. A "lateral axis" is normal to the longitudinal axis and is generally parallel to the plane of the anchor pad 28. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal", which are used to describe the present anchoring system, are used consistently with the description of the exemplifying application. Thus, proximal and distal are used in reference to the catheter's insertion site on the patient (not shown). The term channel is not intended to connote a particular length and may connote a segment or small portion of a channel. Also, the terms "top," "bottom," "upper," and "lower" are used in the context of the orientation of the anchoring system illustrated in FIG. 1, and are not intended to imply a limitation to the orientation that the anchoring system 20 can assume on the patient. A detailed description of the catheterization system (including the present anchoring system), and its associated method of use now follows.

T-Connector

Figure 11:
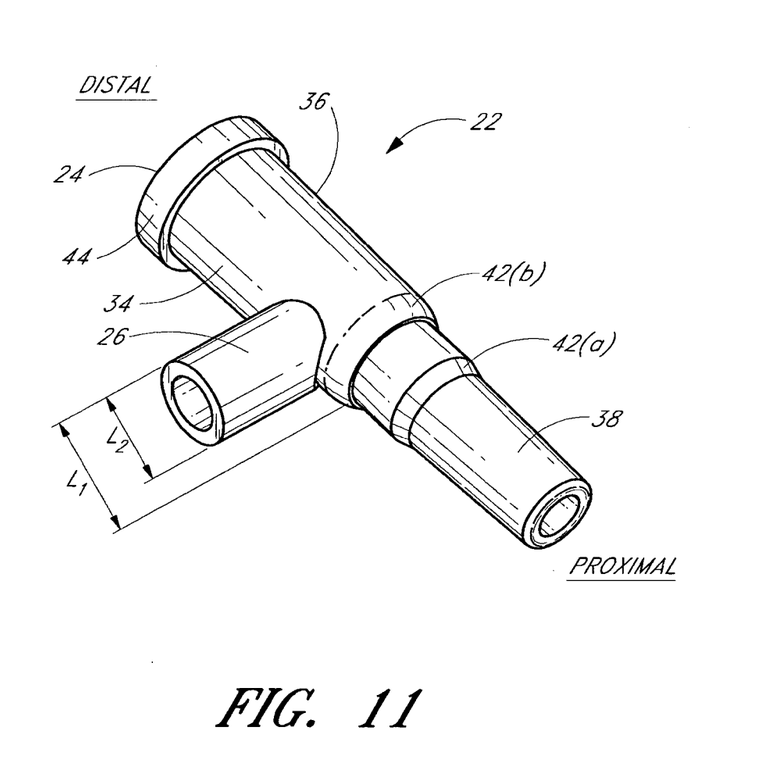
FIG. 11 is a perspective view of a catheter t-connector for use with the catheterization system illustrated in FIG. 1.

As best seen in FIG. 11, the t-connector 22 comprises a first tubular body 34 defined between a proximal end 38 and a distal end 36. A second tubular body or t-fitting 26 connects to the tubular body 34 between the proximal and distal ends of the tubular body 34. The t-fitting 26 and tubular body 34 form a right angle in the illustrated embodiment. However, the t-fitting 26 and tubular body 34 may intersect to form obtuse or acute angles therebetween. For example, an obtuse angle may be selected to closely align the flow paths through the t-fitting 26 and the tubular body 34. In the preferred embodiment, the t-fitting 26 has a cylindrical shape with an outer diameter $L_2$. However, the t-fitting 26 may have other shapes to match a non-cylindrical receiving channel of the retainer 30.

The proximal end 38 is configured to engage the distal end of a hub of a catheter or of any female connector. The proximal end 38 of the t-connector 22 forms a fluid tight seal for fluids to pass from the t-connector 22 and into the catheter. In the illustrated embodiment, the proximal end 38 of the t-connector 22 is configured as a male portion to be inserted into a standard receptacle of a catheter hub. The proximal end 38, however, can be configured to engage other types of catheter connectors. Those skilled in the art can readily select the type of catheter connector to be used with the present anchoring system 20 and can modify the anchoring system according to the teachings of the present invention to suit the particular application (e.g., venous, arterial, epidural, peripheral, etc.).

As seen in FIG. 11, at least a portion of the proximal end 38 has a frusto-conical shape and extends proximally from the tubular body 34. Tapered shoulders 42(a), 42(b) are disposed on the tubular body 34 and between the t-fitting 26 and the proximal end 38. Tapered shoulder 42(b) is spaced a distance $L_1$ from the distal side of the t-fitting 26. A central lumen extends through the tubular body 34 and terminates at an opening at the proximal end 38.

The distal end 36 of the t-connector 22 comprises a needle stick membrane 24 or septum. The needle stick membrane 24 or septum is configured to allow a syringe needle to penetrate through the membrane and into the central lumen. For example, fluids injected into the t-connector 22 via the membrane 24 flow through the fluid tight seal formed between the t-connector 22 and catheter and then into the patient. A distal end of the central lumen terminates at the membrane 24.

The t-fitting 26 is adapted to receive an end of a medical supply tube. In an exemplifying embodiment, at least a portion of the fluid tube is permanently attached to (e.g., embedded within) the end of the t-fitting 26. A second lumen through the t-fitting 26 communicates with the central lumen to allow fluid flowing through the t-fitting 26 to enter the central lumen of the t-connector 22.

Fluids enter the t-connector 22 via the needle stick membrane 24 and the t-fitting 26. The connection between the medical supply tube and the t-fitting 26 forms a first passageway for fluids to enter the t-connector 22. A second passageway into the t-connector 22 if formed through the membrane 24. For example, a healthcare worker using a syringe needle punctures the distally located membrane 24. Once the syringe needle penetrates the membrane 24, the healthcare worker injects the contents of the syringe directly into the first passageway through the connector 22.

With reference to FIGS. 1 and 11, the distal end 36 of the t-connector 22 includes a radially extending member 44 projecting outward from the tubular body 34. In particular, the t-connector 22 can include one or more radially extending members 44 disposed between the distal end 36 and the t-fitting 26. The radially extending member 44 provides a ridge for the healthcare worker to steady a syringe during insertion of the needle through the membrane 24.

Anchor Pad

Figure 2:
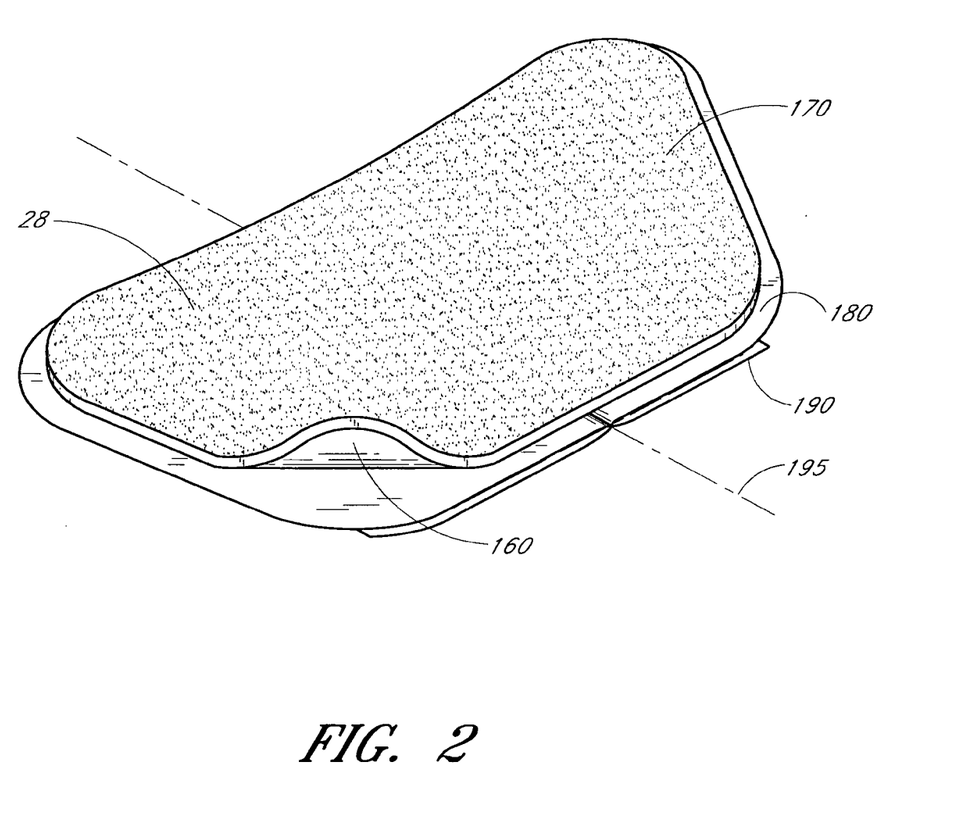
FIG. 2 is a perspective view of an anchor pad of the catheterization system illustrated in FIG. 1.

FIG. 2 illustrates the anchor pad 28 apart from the rest of the securement device 20 shown in FIG. 1. The lower side of the pad 28 faces toward the skin of the patient, and is preferably covered with an adhesive surface suitable for attaching the anchor pad 28 to the skin of the patient. The entire surface, however, need not be covered. An upper surface 170 of the anchor pad 28 faces away from the skin of the patient and supports the retainer 30. The anchor pad 28 comprises a generally trapezoidal shape. Although only a single shape of the anchor pad is illustrated in FIG. 2, those of skill in the art will recognize that a variety of shapes can be used.

The anchor pad 28 desirably comprises a laminate structure with an upper plastic, paper or foam layer (e.g., closed-cell polyethylene foam) and a lower adhesive layer. The lower adhesive layer constitutes a lower surface 160 of the anchor pad. The lower surface 160 desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pad 28 can include suture holes in addition to the adhesive layer to further secure the anchor pad to the patient's skin.

In other variations, a hydrocolloid adhesive or zinc oxide-based adhesive can advantageously be used upon the anchor pad 28 for attaching the anchor pad to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

A surface of the upper foam layer constitutes an upper surface 170 of the anchor pad 28. The upper surface 170 can be roughened by corona-treating the foam with a low electric charge. The roughened or porous upper surface can improve the quality of the adhesive joint (which is described below) with the bottom surface of the retainer 30.

A removable paper or plastic release liner 180 desirably covers the adhesive lower surface 160 before use. The liner 180 preferably resists tearing and desirably is divided into a plurality of pieces to ease attachment of the pad to a patient's skin.

The liner 180 comprises a folded over portion to define a pull tab 190. The pull tab 190 can be utilized to remove the paper or plastic release liner 180 from the adhesive lower surface 160 before use. A healthcare provider uses the pull tab 190 by grasping and pulling on it so that the liner 180 is separated from the lower surface 160. The pull tab 190 overcomes any requirement that the healthcare provider pick at a corner edge or other segment of the liner 180 in order to separate the liner 180 from the adhesive layer.

The pull tab 190 of course can be designed in a variety of configurations. For example, the pull tab 190 can be located along a center line of the anchor pad 28; or alternatively, the pull tab can be located along any line of the anchor pad 28 in order to ease the application of the anchor pad 28 onto the patient's skin at a specific site. For example, an area of a patient's skin with an abrupt bend, such as at a joint, can require that the pull tab 190 be aligned toward one of the lateral ends of the anchor pad 28 rather than along the center line. In the embodiment illustrated in FIG. 2, the fold forming the pull tab 190 is located along a centerline 195.

In another variation, the anchor pad 28 comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface 160 of the anchor pad.

Retainer

FIGS. 3 through 10 illustrate the retainer 30, which is configured in accordance with a preferred embodiment of the present invention. The retainer 30 has a body 50 that defines a central or first channel 52 disposed above a base surface 54. The channel 52 extends about a central, longitudinally extending axis C and has an opening 56 that faces away from the base surface 54. The proximal and distal ends of the channel 52 also open through the ends of the retainer body 50. A radius of curvature for the channel 52 preferably matches or at least approximates the radius of the portion of the connector tubular body 34 to be retained. In a preferred embodiment, at least a portion of the first channel 52 has a lateral width that is smaller than a maximum diameter of the connector tubular body 34, as described below in greater detail.

The retainer further includes a second channel 29 which intersects with the first channel 52. The second channel 29 extends about a laterally extending axis D and has an opening 88 that faces away from the base surface 54. The first channel 52 includes a first channel segment and a second channel segment disposed on opposite sides of the axis D. The second channel 29 has a first channel segment and a second channel segment disposed on opposite sides of the axis C. The lateral ends of the second channel 29 open through the sides of the retainer body 50. A radius of curvature for the second channel 29 preferably matches or at least approximates the radius of the portion of the t-fitting 26 to be retained. In a preferred embodiment, at least a portion of the second channel 29 has a longitudinal width that is smaller than a maximum diameter of the t-fitting 26.

Figure 8:
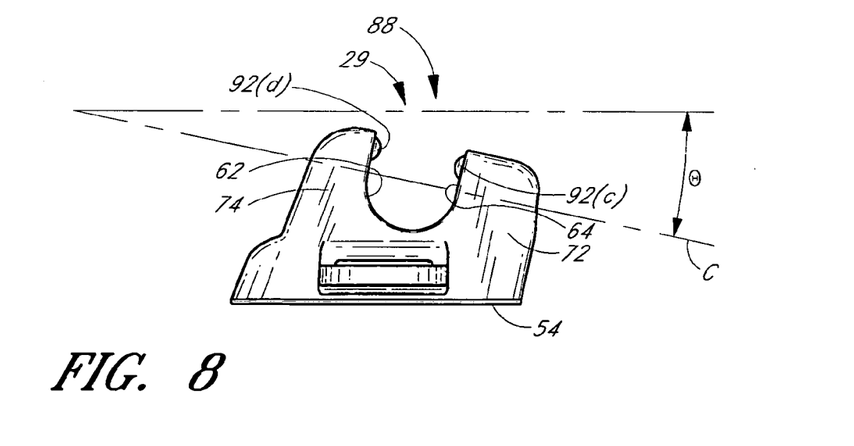
FIG. 8 is an elevational side view of the retainer of FIG. 3.

FIG. 8 illustrates the channel axis C skewed relative to a base surface 54 of the retainer 30. An incident angle θ defined between the base surface 54 and the channel axis C preferably is less than 45°. More preferably, the incident angle θ ranges between 5° and 30°. In an exemplifying embodiment for intravenous use, the angle θ preferably equals approximately 7°. In another exemplifying embodiment for arterial use, the incident angle θ preferably equals about 22°.

As best seen in FIGS. 3, 4, 8 and 9, the retainer 30 also includes a plurality of abutment surfaces that extend laterally from the channel 52. Each abutment surface lies generally normal to the central axis C of the channel 52. These abutment surfaces include a proximal-most abutment surface 60, a distal-most abutment surface 62 and an intermediate surface 64. The abutment surfaces capture both the first tubular body 34 and the second tubular body 26 within the retainer 30 so as to arrest movement of the medical article relative to the retainer. The proximal-most abutment surface 60 is defined by a protruding wall from the inside circumference of the first channel 52 at the proximal end of the retainer 30. The distal-most abutment surface 62 and the intermediate surface 64 lie between the proximal-most abutment surface 60 and the distal end of the retainer 30.

As shown most clearly in FIG. 8, the distal-most abutment surface 62 and the intermediate surface 64 are defined by an inside surface of the second channel 29. The proximal- and distal-most abutment surfaces 60, 62 preferably are separated by a distance that is generally equal to the longitudinal length between the shoulder 42(b) of the connector tubular body 34 and a distal surface of the t-fitting 26. This distance is illustrated as $L_1$ in FIG. 11. The proximal-most abutment surface 60 contacts with the shoulder 42(b) of the connector fitting 22 to inhibit proximal, longitudinal motion of the connector fitting relative to the retainer 30. The distal-most abutment surface 62 contacts with the distal surface of the t-fitting 26 to inhibit distal, longitudinal motion of the connector fitting 22 relative to the retainer 30. Together, the proximal and distal-most abutment surfaces 60, 62 inhibit movement of the retainer in both longitudinal directions. However, a single abutment surface may be used independently to arrest movement in the proximal or distal direction. Alternatively, the first channel 52 can have a tapering shape which, together with a single abutment surface, arrests longitudinal movement in the proximal and distal directions. In a variation of the retainer 30, the proximal-most abutment surface 60 can be omitted when the distal-most abutment surface 62 and the intermediate surface 64 are defined by a distance that is generally equal to the outer diameter of the second channel 29. This distance is illustrated as $L_2$ in FIG. 11. In such an embodiment, the proximal and distal portions of the t-fitting 26 cooperate with the proximal and distal sides of the lateral channel 29 to arrest all longitudinal movement of the t-connector 22 relative to the retainer 30.

Figure 3:
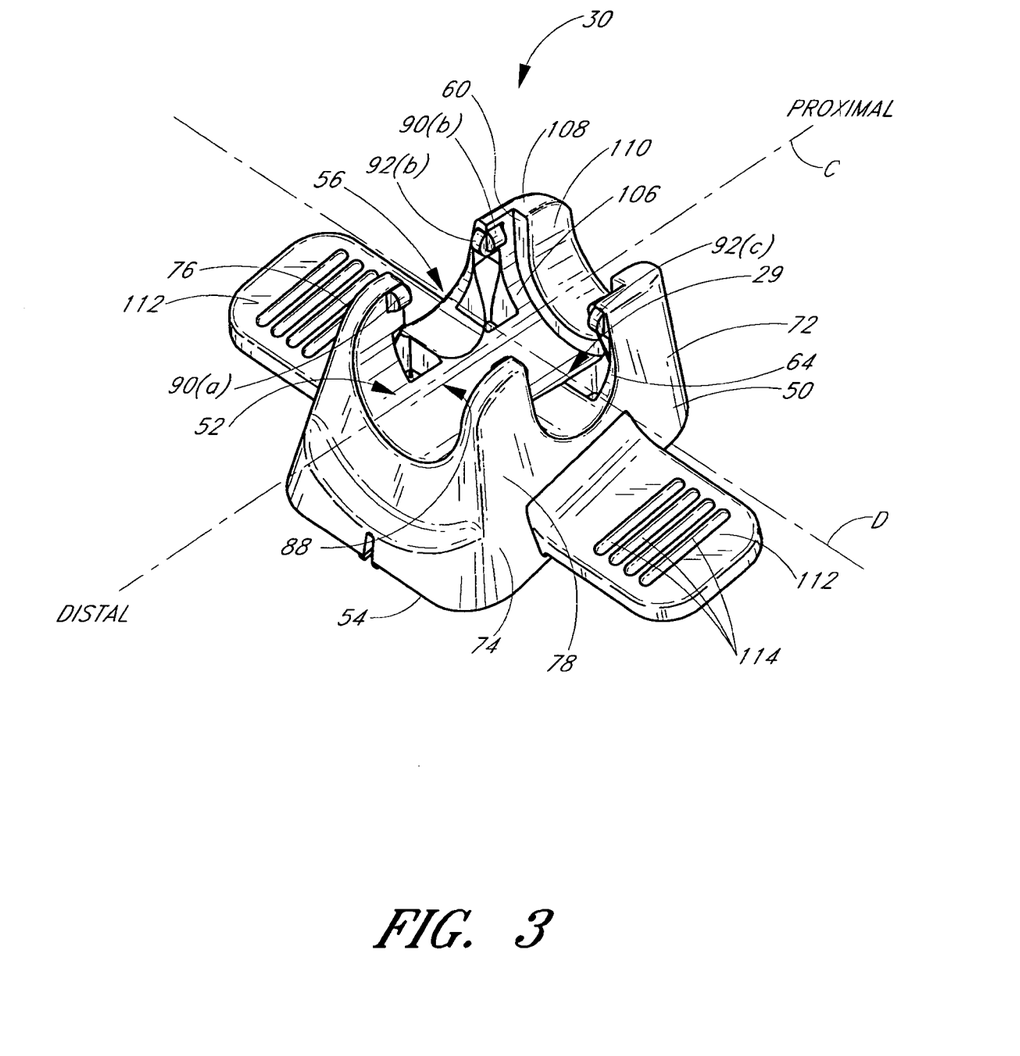
FIG. 3 is a perspective view of a retainer of the catheterization system of FIG. 1.

As seen in FIG. 3, the retainer body 50 includes proximal and distal body portions 72, 74, respectively. The first channel 52 extends through these body portions 72, 74 and is open at each of its ends through end walls of the proximal and distal body portions 72, 74.

As seen in FIG. 3, the retainer body 50 includes lateral side portions 76, 78. The lateral channel 29 extends through these portions 76, 78 and is open at each of its ends through side walls of the lateral side portions 76, 78.

The retainer 30 has a plurality of protuberances defined by the intersection of the second channel 29 and the first channel 52. Protuberance pairs 90(a), 90(d) and 90(b), 90(c) are arranged on opposing sides of the distal and proximal portions 76, 78, respectively. The protuberances 90 extend generally toward the central axis C of the first channel 52. Thus, the protuberances 90 reduce the lateral width of the channel opening 52 as defined between the opposing walls of channel 52. In this manner, each pair of opposing protuberances 90 either grip onto or at least extend over an upper section of the connector tubular body 34 to inhibit unintentional transverse movement of the t-connector 22 once situated within the retainer 30.

Figure 4:
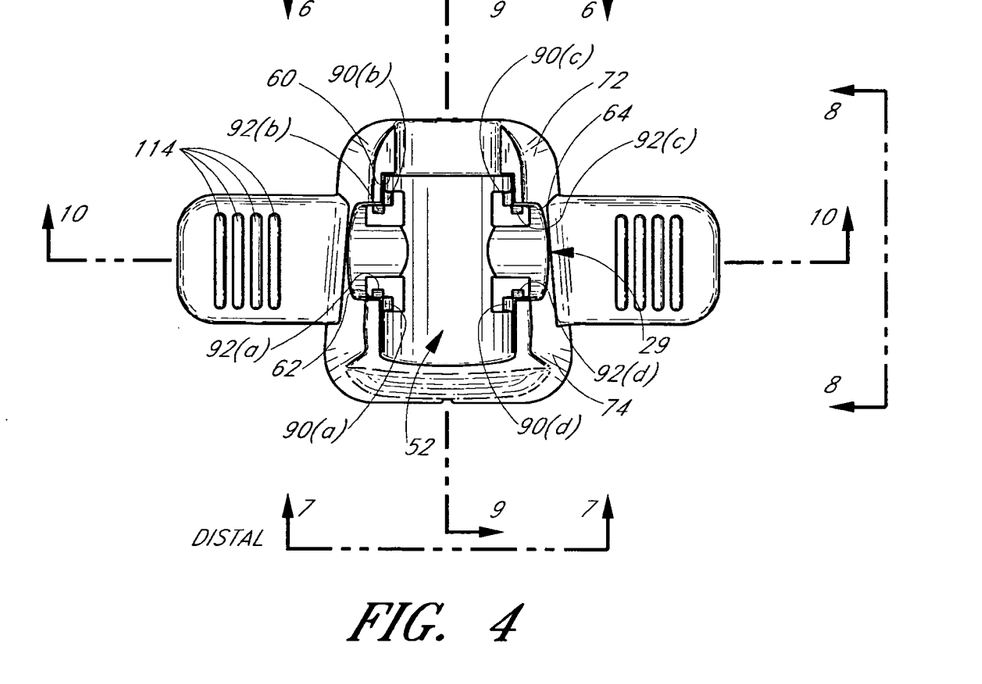
FIG. 4 is a top plan view of the retainer of FIG. 3.
Figure 9:
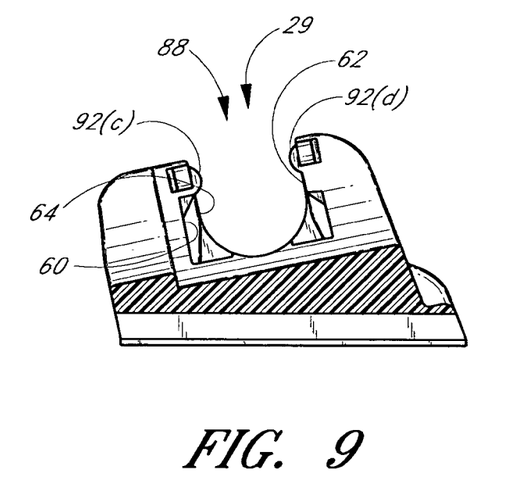
FIG. 9 is a cross-sectional view of the retainer of FIG. 4, taken along line 9-9.

The walls of the second channel 29 further inhibit unintentional transverse movement of t-connector 22. For this purpose, the second channel 29 has a plurality of protuberances which are defined by the intersection of the second channel 29 and the first channel 52. As seen in FIGS. 4, 8 and 9, protuberance pairs 92(a), 92(b) and 92(c), 92(d) are arranged on opposite sides of the second channel 29. The protuberances 92 extend generally toward the central axis D of the second channel 29. The protuberances 92 reduce the lateral width of the channel opening 88 as defined between the opposing walls of the second channel 29. Each pair of opposing protuberances 92 is configured to either grip onto or at least extend over an upper section of the t-fitting 29 to inhibit unintentional transverse movement of the t-fitting 26 once situated within the retainer 30. The retainer 30 can have one or both protuberances pairs 92(a), 92(b) and 92(c), 92(d). To inhibit transverse movement, the t-fitting 29 is placed between one of the protuberance pairs 92(a), 92(b) and 92(c), 92(d) depending on the orientation of the medical supply tube attached to the t-fitting 26. Each pair of opposing protuberances 92 can further arrest rotation of the t-connector 22 about the longitudinal C axis.

The channels 29, 52 have a generally U-shaped cross-sectional shape. However, the protuberances 90, 92 extend generally toward the central axis of their respective channels. Thus the protuberances 90, 92 reduce the lateral widths of their respective channel openings 56, 88 as defined between the opposing walls of each channel. In this manner, each pair of opposing protuberances 90, 92 either grip onto or at least extend over an upper section of the connector 22 to inhibit unintentional transverse movement once the t-connector 22 is situated within the retainer 30.

Alternatively, one or both of the channels 29, 52 can have a truncated, circular cross-sectional shape that extends through an arc of greater than 180°. In an exemplifying embodiment, the first channel 52 extends through an arc of about 200° about the channel axis C. The first channel 52, in cross-section, thus may extend through an arc of a little more than 180° about the channel axis C such that the lateral width of the opening 56 is slightly smaller than the overall diameter of the first channel 52. This allows for the t-connector 22 to be snapped into the first channel 52. With such an arrangement, transverse movement can be inhibited when using a retainer 30 that does not include protuberances 90.

Figure 10:
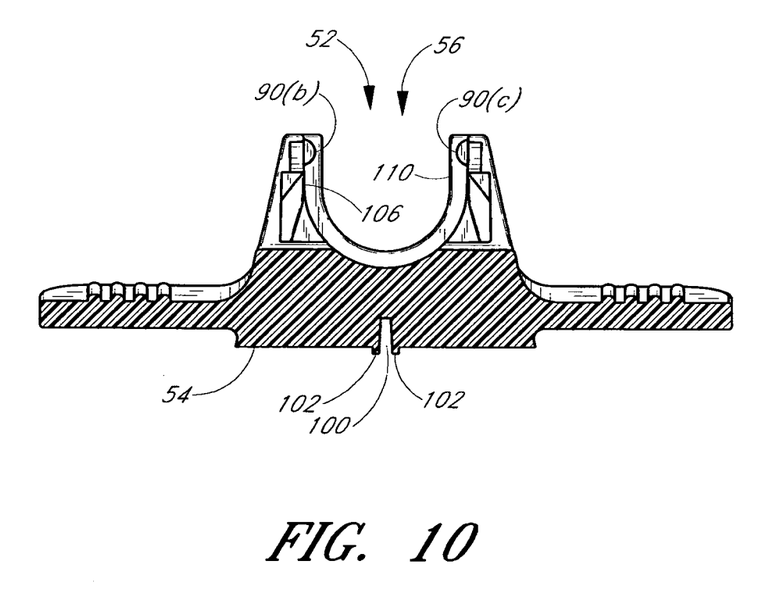
FIG. 10 is a cross-sectional view of the retainer of FIG. 4, taken along line 10-10.

As best seen in FIGS. 9 and 10, the upper side surfaces of the protuberances 90, 92 preferably are rounded or chamfered and slop toward the channel opening 56, 88 to guide the connector tubular body 34 and the t-fitting 26 into their respective channels 29, 52. As a result, the t-connector 22 slides more smoothly over the protuberances 90, 92 and into the channels as the opposing walls of the channels 29, 52 are deflected outwardly by the interference with the t-connector 22 during the insertion process. A two step insertion process can also be used. For example, the t-connector 22 is rotated about the longitudinal axis C so that the passageway through the t-fitting 26 is parallel to the transverse axis while the tubular body 34 is aligned with the first channel opening 56. The aligned tubular body 34 is inserted through the channel opening 56 and into the first channel 52. Once inserted the protuberances 90 grip onto or at least extend over an upper section of the tubular body 34. The t-connector 22 is then rotated about the longitudinal axis C so that the passageway through the t-fitting 26 is parallel to the laterally extending axis D. As the connector 22 is rotated about the longitudinal C-axis, the t-fitting 26 passes between the protuberances 92 and enters through the channel opening 88 and into the second channel 29. Once rotated, the protuberances 92 grip onto or at lest extend over an upper section of the t-fitting 26 to thereby inhibit rotational and transverse movement of the t-connector 22.

In a preferred mode, the proximal and/or distal body portions 72, 74 have sufficient lengths to prevent the connector 22 from yawing (i.e., movement side to side in a longitudinal-lateral plane). That is, the length of the proximal or distal body portion 72, 74, which interacts with the t-connector 22 is sufficient so that the portion does not act as a fulcrum. However, while such wall length is preferred, the wall length can be significantly shorter (e.g., interact with the connector at a single longitudinal point) where the connector body 34 is also held near the opposite end (i.e. proximal or distal end).

As seen in FIG. 10, the retainer 30 also includes a groove 100 that extends longitudinally along the base surface 54 and beneath at least a portion of the first channel 52. In the illustrated embodiment, the groove 100 runs along the entire longitudinal length of the retainer 30. The lateral width of the groove 100 is less than the diameter of the first channel 52.

Figure 6:
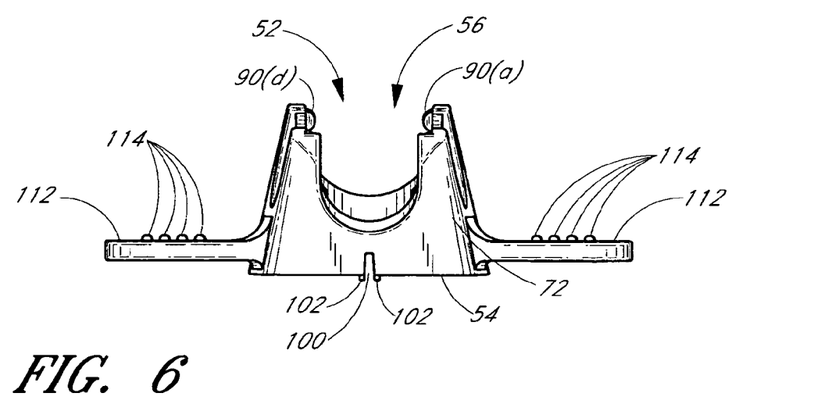
FIG. 6 is an elevational proximal end view of the retainer of FIG. 3.
Figure 7:
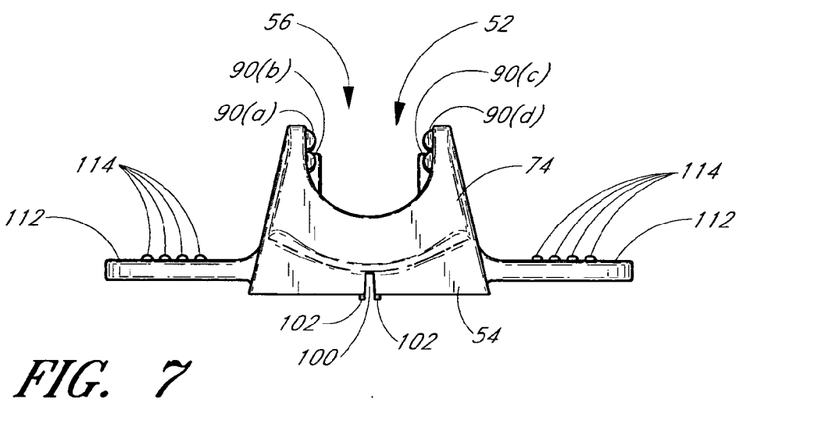
FIG. 7 is an elevational distal end view of the retainer of FIG. 3.

As seen in FIGS. 6, 7 and 10, a pair of ridges 102 flank the groove 100. Each ridge 102 extends slightly below the base surface 54 to inhibit an influx of adhesive into the groove 100 when the retainer is attached to the anchor pad 28.

Figure 5:
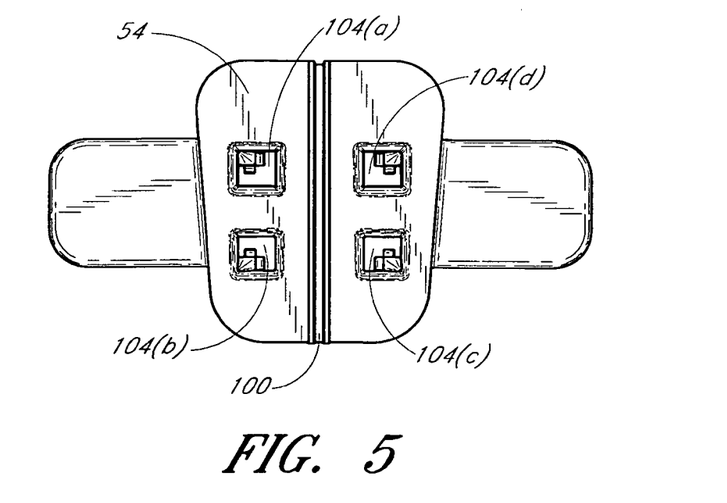
FIG. 5 is a bottom plan view of the retainer of FIG. 3.

As seen in FIGS. 4 and 5, recesses 104(a), 104(b), 104(c), and 104(d) are defined in the retainer body 50 at the four intersection points of the first channel 52 with the second channel 29, and extend toward the base surface 54 from the bottom surfaces of the channels 29, 52. In the illustrated embodiment, the recesses 104 extend between the first channel 52 and the base surface 54 in order to reduce the material weight of the retainer 30.

The proximal body portion 72 defines a proximal channel segment 106 of the first channel 52. The proximal channel segment 106 is disposed between the proximal sides of the protuberances 90(b), 90(c) and the proximal-most abutment surface 60. The proximal channel segment 106 generally has a U-shaped cross-section with a radius of curvature at least as large as the minimum radius of the connector tubular body 34.

The proximal body portion 72 also includes a proximal upstanding wall 108 that extends laterally across the proximal end of the retainer 30. The upstanding wall 108 includes a U-shaped opening 110 that defines the proximal end of the first channel 52. In the illustrated embodiment, the opening 110 has a lateral width that is smaller than the diameter of the distal end 36 of the t-connector 22, but is larger than the diameter of the proximal end 38 of the t-connector 22. The proximal upstanding wall 108 defines the proximal-most abutment surface 60 on its distal side. The proximal-most abutment surface 60 thus, in the illustrated embodiment, lies at the proximal end of the proximal channel segment 106 and at the distal end of the upstanding wall 108.

Both the proximal opening 110 and the proximal channel segment 106 of the channel 52 have generally U-shapes; however, one or both of these channel segments can have, for example, a truncated, generally circular shape. In this variation, the opening 110 or the proximal channel segment 106 can receive the proximal end 38 of the connector tubular body 34, in a snap fit manner to inhibit further transverse movement of the t-connector 22 relative to the retainer 30. It is preferred, however, that these channel segments do not so engage the connector body in order to ease the insertion process, as described below.

As illustrated in FIG. 3, the retainer 30 includes finger platforms 112 on both sides of the first channel 52. Each finger platform 112 extends laterally from one side of the retainer 30 at a location slightly above the base surface 54. Each finger platform 112 also has a ribbed upper surface 114 to improve frictional contact between a healthcare provider's fingers and the platform 112. The finger platforms 112 are sized and configured to allow a healthcare provider to press the anchoring system 20 against the skin of the patient while pulling up on the t-connector 22 when disengaging the t-connector 22 from the retainer 30.

The combination of the finger platforms 112 and the groove 100 along the base surface 54 beneath the first channel 52 makes it easier for the healthcare provider to open the first channel 52 to a sufficient degree so as to insert the connector tubular body 34 into the first channel 52.

The retainer 30 is made of relatively stiff plastic material (e.g., polycarbonate), but is somewhat flexible such that the t-connector 22 will force the protuberances 90 of the distal and proximal body portions 72, 74 outwardly when a healthcare provider presses the t-connector 22 into the first channel 52 of the retainer 30. When the t-connector 22 sits in the first channel 52, the protuberances 90 of the first channel 52 snap inwardly to their original position to securely hold the t-connector 22 within the retainer 30. The connector is rotated about the longitudinal axis C until the t-fitting 26 contacts protuberances 92. The flexibility of the retainer 30 allows the healthcare provider to press the t-connector 22 into the second channel 29. When the t-connector 22 sits in the second channel 29, the protuberances 92 of the second channel 29 snap inwardly to their original position to further securely hold the t-connector 22 within the retainer 30.

The retainer 30 may be constructed in any of a variety of ways which will be well known to one of skill in the art. For instance, the retainer 30 may be integrally molded such as by injection molding or by thermoplasty. The retainer 30 preferably comprises a durably, flexible material, and more preferably comprise a generally inert, non-toxic material. Suitable materials include plastics, polymers, or composites such as polypropylene, polyethylene, polycarbonate, polyvinylchloride, polyurethane, tetrafluoroethylene (e.g., TEFLON®), polytetrafluoroethylene (a.k.a., PTEF), acetal resin (e.g., DELRIN®), chlorotrifluoroethylene (e.g., KEL-F®), acrylonitrile butadiene styrene, styrene butadiene, nylon, olefin, acrylic, polyester, moldable silicon, thermoplastic urethane, thermoplastic elastomers, thermoset plastics and the like. The retainer 30 is preferably formed by injection molding using a polycarbonate, available commercially from GE Plastics. However, other materials can be used.

Method of Use

The following discussion of the method of use will be with reference to FIGS. 1 and 11-14, and will be in the context of intravenous catheterization. As the following discussion will illustrate, however, it is understood that the anchoring system 20 can be used in other catheterization procedures as well. The discussion of the method of use is intended to augment the above description of the preferred embodiments, and, thus, should be read together. In order to illustrate more clearly the interaction between the retainer 30 and the t-connector 22 in this embodiment, the anchor pad 28 of the anchoring system 20 is illustrated as detached from the retainer. In accordance with the preferred embodiment, however, the entire anchoring system 20 is assembled in accordance with the above-description (e.g., the anchor pad is attached to the retainer) and is sterilized before use.

A healthcare provider typically begins the catheterization process by positioning the catheter at a desired location above a vein. The healthcare provider introduces a needle or other stylus through a cannula portion of the catheter and into the skin of the patient at a desired angle of incident. For intravenous use, the catheter commonly has an incident angle of approximately 7°. The healthcare provider then inserts the cannula of the catheter into the patient and withdraws the needle or stylus. Part of the catheter remains exposed above the skin. The healthcare provider inserts the proximal end 38 of the t-connector 22 into the catheter hub (not shown). The healthcare provider then securely attaches the t-connector 22 to the catheter by engaging, for example, a spin nut with the catheter hub in a known manner.

Figure 12:
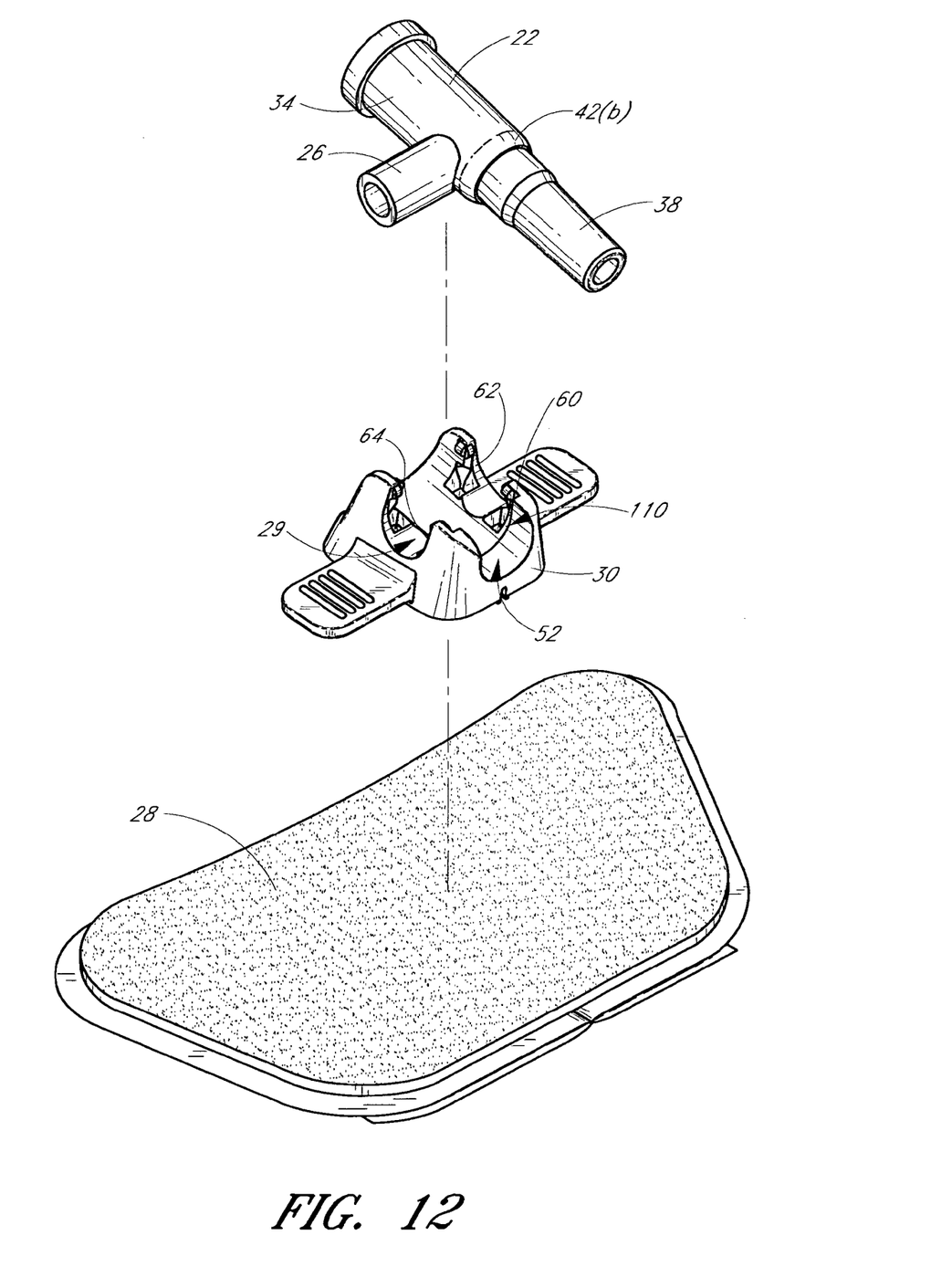
FIG. 12 is an exploded, perspective view of the t-connector fitting aligned with the anchor pad and the retainer of FIG. 1.
Figure 13:
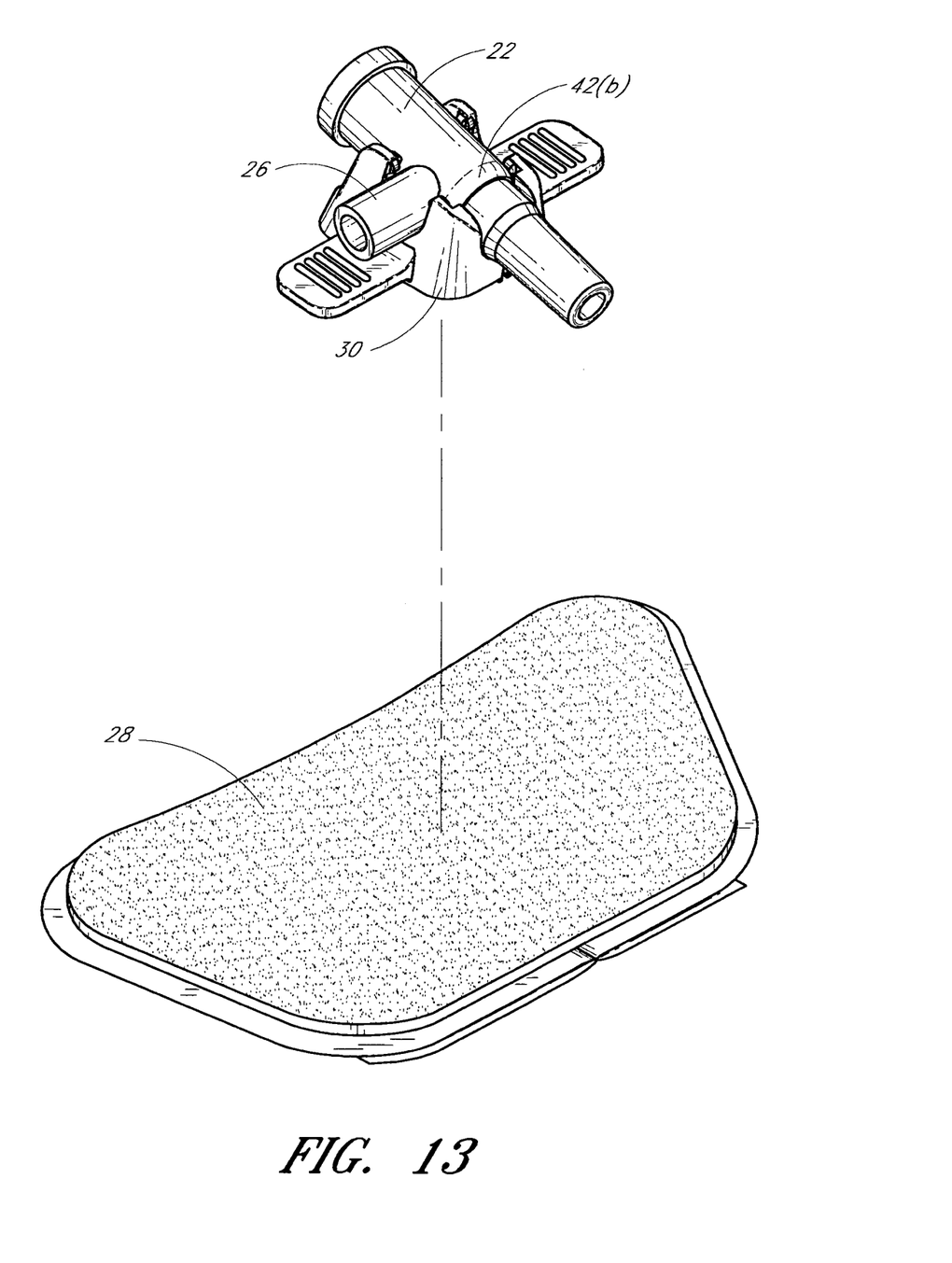
FIG. 13 is an exploded, perspective view of the t-connector fitting being inserted into the retainer of FIG. 1.

The healthcare provider positions the retainer 30 below the t-connector 22 and inserts a portion of the proximal end 38 through the proximal opening 110. At this point, the axis of the t-connector 22 is skewed relative to the axis C of the first channel 52. The healthcare provider pulls the t-connector 22 proximally (or conversely slides the retainer distally) until the tapered shoulder 42(b) of the connector tubular body 34 contacts the proximal-most abutment surface 60. This act registers the longitudinal position of the t-connector 22 with the retainer 30 to align the t-connector 22 above the retainer 30. So positioned, the longitudinal midpoint of the t-fitting 26 of the t-connector 22 is aligned with the longitudinal midpoint of the second channel 29 of the retainer 30 and with the longitudinal midpoint between the intermediate surface 64 and the distal-most abutment surface 62. The healthcare provider then presses the t-connector 22 into the first channel 52 of the retainer 30. In doing so, the t-connector 22 is pressed between the protuberances 90 of the distal and proximal body portions 72, 74 of the retainer 30. As the healthcare provider presses the t-connector 22 into the retainer 30, the t-fitting 29 is rotated and generally guided into the space between the intermediate surface 64 and the distal-most abutment surface 62. Alternatively, the t-fitting 29 is rotated after the t-connector 22 is secured in the first channel 52.

As mentioned above, the opening 56 of the first channel 52 at the longitudinal locations of the protuberances 90 has a smaller width measured in the lateral direction than the diameter of the connector tubular body 34 at those locations. The distal and proximal body portions 74, 72 thus deflect outwardly in a lateral direction. Once the tubular body 34 of the t-connector 22 rests within the first channel 52 of the retainer 30, the protuberances 90 spring back to snap the t-connector 22 in place. The first channel 52 and protuberances 90 of the retainer 30 thus prevent unintentional transverse and lateral movement of the t-connector 22. The protuberances 92 further prevent unintentional rotational and transverse movement of the t-connector 22.

Figure 14:
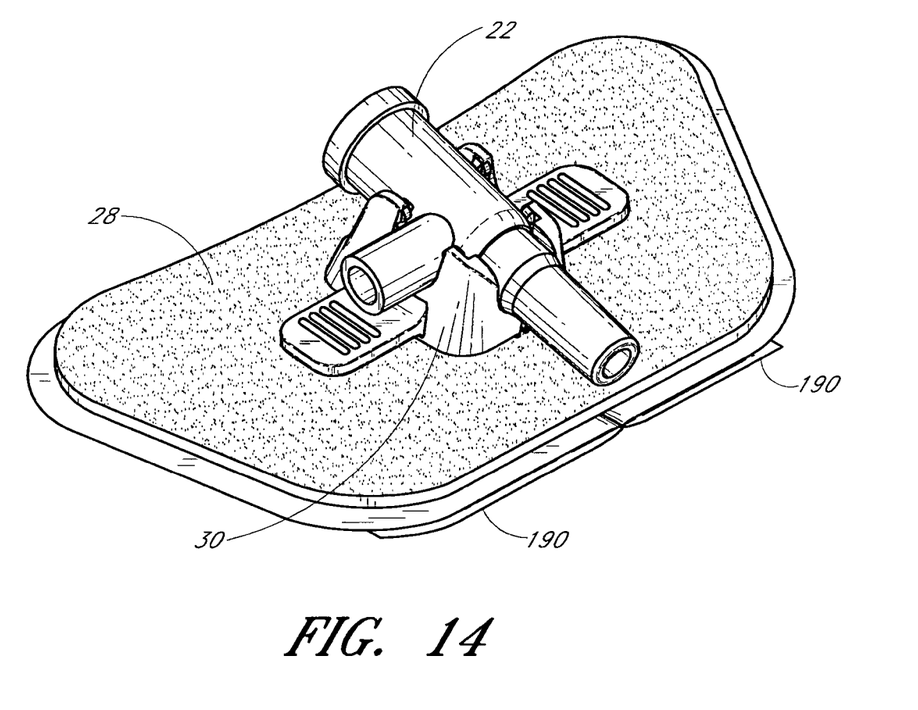
FIG. 14 is a perspective view of the t-connector fitting secured to the securement device of FIG. 1.

Once the t-connector 22 is secured in the retainer 30, the healthcare provider removes the liner 180 which initially covers the adhesive lower surface 160 of the anchor pad 28. The healthcare provider attaches the pad 28 to the patient's skin proximate to the indwelling catheter. Specifically, the healthcare provider grips one of the two pull tabs 190. The healthcare provider then pulls on the tab 190 and peels the backing off one side of the bottom adhesive layer. The healthcare provider positions the anchor pad 28 over the placement site and places the exposed bottom layer against the patient's skin to adhere the anchor pad 28 to the patient. Light pressure over the upper surface 170 assures good adhesion between the anchor pad 28 and the patient's skin. The anchor pad 28, due to its flexibility, contours to the contours of the topical surface to which the anchor pad 28 adheres.

The healthcare provider repeats this procedure for the other side of the lower surface of the anchor pad 28. Alternatively, the healthcare provider may completely remove the liner 180 from the pad 28 before attaching the pad 28 to the patient's skin. Additionally, the anchor pad 28 can be attached to the patient before the t-connector 22 is inserted into the retainer 30.

The present anchoring system thus provide a sterile, tight-gripping, needle- and tape-free way to anchor a medical article to a patient. The retainer eliminates use of tape, and if prior protocol required suturing, it also eliminates accidental needle sticks, suture-wound-site infections and scarring. In addition, the retainer can be configured to be used with any of a wide variety of catheters, fittings, tubes, wires, and other medical articles. Patient comfort is also enhanced and application time is decreased with the use of the present anchoring system.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct anchoring systems in accordance with principles of the present invention.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present retainer has been described in the context of particularly preferred embodiments, the skilled artisan will appreciate, in view of the present disclosure, that certain advantages, features and aspects of the retainer may be realized in a variety of other applications, many of which have been noted above. For example, while particularly useful for small-scale applications, such as the illustrated medical application, the skilled artisan can readily adopt the principles and advantages described herein to a variety of other applications, including larger scale devices. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. An anchoring system for securely anchoring to a patient a medical article of the type having an elongated body including first and second elongated tubular bodies, the second elongated tubular body intersecting with the first elongated tubular body, the anchoring system comprising:
a retainer including a body and first and second channels extending through at least a portion of the body, the channels being configured to accept at least a portion of the first and second elongated tubular bodies of the medical article, and means for capturing both the first and second tubular bodies within the retainer body so as to arrest at least rotational movement of the medical article in both directions about a longitudinal axis relative to the retainer; and
an anchor pad having two sides, the retainer being mounted on one side and the other side including a layer of adhesive.

2. The anchoring system of claim 1, wherein at least a section of the second channel is generally U-shaped.

3. The anchoring system of claim 1 additionally comprising a pair of laterally extending platforms, and a longitudinal groove that extends parallel to the axis of the first channel and runs along a bottom surface of the body.

4. A retainer for securing a t-connector including at least first and second tubular members in flow communication with one another, the retainer comprising:
a first channel for receiving the t-connector without regard to the orientation of the second tubular member so that the second tubular member may be in any of a plurality of radial positions with respect to an axis through the first channel, the second tubular member being in a first position of the plurality of positions, being in a second position of the plurality of positions when rotated from the first position by approximately 180 degrees, and being in a third position of the plurality of positions when rotated from the first position by approximately 90 degrees;
a first pair of abutment surfaces longitudinally restraining the first tubular member in both longitudinal directions when the second tubular member is in the first position;
a first pair of protuberances disposed between the first pair of abutment surfaces so as to at least inhibit rotation of the medical article about a longitudinal axis;
a second pair of abutment surfaces longitudinally restraining the first tubular member in both longitudinal directions when the second tubular member is in the second position, the second pair of abutment surfaces being different than the first pair of abutment surfaces; and
an abutment surface longitudinally restraining the first tubular member in a longitudinal direction when the second tubular member is in the third position, the abutment surface being different than the first and second pairs of abutment surfaces.

5. The retainer of claim 4 further comprising a first channel segment and a second channel segment disposed on opposite sides of the axis, wherein the first pair of abutment surfaces are defined by the first channel segment, and the second pair of abutment surfaces are defined by the second channel segment.

6. The retainer of claim 4, wherein the abutment surface is formed along the first channel and lies generally normal to the axis.

7. The retainer of claim 4 additionally comprising one or more protuberances that projects inwardly to reduce a width of the first channel and restrain the t-connector from moving transversely with respect to the retainer.

8. The retainer of claim 7, wherein the one or more protuberances deflect to open the first channel to a size sufficient to receive the first tubular member and return to an undeflected position to restrain the first tubular member in the first channel against unintentional transverse movement.

* * * * *